US009862893B2

(12) United States Patent
Gray et al.

(10) Patent No.: US 9,862,893 B2
(45) Date of Patent: Jan. 9, 2018

(54) PROCESS FOR PURIFYING LIGNOCELLULOSIC FEEDSTOCKS

(75) Inventors: Matthew Gray, Madison, WI (US); Megan Matthes, Madison, WI (US); Thomas Nelson, Sun Prairie, WI (US); Andrew Held, Madison, WI (US)

(73) Assignee: Virent, Inc., Madison, WI (US)

( * ) Notice: Subject to any disclaimer, the term of this patent is extended or adjusted under 35 U.S.C. 154(b) by 825 days.

(21) Appl. No.: 13/469,906

(22) Filed: May 11, 2012

(65) Prior Publication Data

US 2012/0289692 A1 Nov. 15, 2012

Related U.S. Application Data

(60) Provisional application No. 61/485,320, filed on May 12, 2011.

(51) Int. Cl.
| C07H 1/08 | (2006.01) |
| C10G 17/02 | (2006.01) |
| C13K 1/02 | (2006.01) |
| C13K 1/06 | (2006.01) |
| C13K 13/00 | (2006.01) |
| C10G 3/00 | (2006.01) |

(52) U.S. Cl.
CPC ............... *C10G 17/02* (2013.01); *C10G 3/00* (2013.01); *C13K 1/02* (2013.01); *C13K 1/06* (2013.01); *C13K 13/002* (2013.01); *C13K 13/007* (2013.01); *C10G 2300/1014* (2013.01); *C10G 2300/20* (2013.01); *C10G 2300/201* (2013.01); *C12P 2201/00* (2013.01); *Y02E 50/16* (2013.01); *Y02P 30/20* (2015.11)

(58) Field of Classification Search
None
See application file for complete search history.

(56) References Cited

U.S. PATENT DOCUMENTS 5,350,714 A * 9/1994 Trefonas, III ............. G03F 7/16
                                                    210/660
5,518,628 A * 5/1996 Carey ..................... B01J 47/04
                                                    210/686

(Continued)

FOREIGN PATENT DOCUMENTS

| WO | 2007056191 A2 | 5/2007 |
| WO | 2008019468 A1 | 2/2008 |

(Continued)

OTHER PUBLICATIONS

PCT International Search Report and Written Opinion, PCT/US2012/037588, dated Sep. 14, 2012.

*Primary Examiner* — Michael H Wilson
*Assistant Examiner* — Katherine Will
(74) *Attorney, Agent, or Firm* — Quarles & Brady LLP

(57) ABSTRACT

The present invention includes methods for removing mineral acids, mineral salts and contaminants, such as metal impurities, ash, terpenoids, stilbenes, flavonoids, proteins, and other inorganic products, from a lignocellulosic feedstock stream containing organic acids, carbohydrates, starches, polysaccharides, disaccharides, monosaccharides, sugars, sugar alcohols, phenols, cresols, and other oxygenated hydrocarbons, in a manner that maintains a portion of the organic acids and other oxygenated hydrocarbons in the product stream.

20 Claims, 6 Drawing Sheets

(56) References Cited

U.S. PATENT DOCUMENTS

| | | | |
|---|---|---|---|
| 5,536,325 A * | 7/1996 | Brink | B02C 13/18 |
| | | | 127/37 |
| 6,699,457 B2 | 3/2004 | Cortright et al. | |
| 6,709,527 B1 | 3/2004 | Fechter et al. | |
| 6,911,481 B2 * | 6/2005 | Tanaka | B01J 49/00 |
| | | | 210/675 |
| 6,953,873 B2 | 10/2005 | Cortright et al. | |
| 6,964,757 B2 | 11/2005 | Cortright et al. | |
| 7,767,867 B2 | 8/2010 | Cortright | |
| 7,919,658 B2 * | 4/2011 | Adkesson | B01D 61/027 |
| | | | 568/868 |
| 7,977,517 B2 | 7/2011 | Cortright et al. | |
| 8,017,818 B2 | 9/2011 | Cortright et al. | |
| 8,053,615 B2 | 11/2011 | Cortright et al. | |
| 2007/0112187 A1 | 5/2007 | Heikkila et al. | |
| 2009/0211942 A1 | 8/2009 | Cortright et al. | |
| 2010/0076233 A1 | 3/2010 | Cortright et al. | |
| 2010/0228062 A1 | 9/2010 | Babicki et al. | |
| 2010/0256428 A1 | 10/2010 | Marker et al. | |
| 2010/0287826 A1 * | 11/2010 | Hoffman | C10L 5/363 |
| | | | 44/605 |
| 2014/0087432 A1 * | 3/2014 | Nguyen | C12P 19/14 |
| | | | 435/99 |

FOREIGN PATENT DOCUMENTS

| | | | | |
|---|---|---|---|---|
| WO | WO 2008019468 A1 * | 2/2008 | | B01D 15/363 |
| WO | WO 2011057413 A1 * | 5/2011 | | C07G 1/00 |

* cited by examiner

PROCESS FOR PURIFYING LIGNOCELLULOSIC FEEDSTOCKS

CROSS-REFERENCE TO RELATED APPLICATION

This application claims the benefit of U.S. Provisional Application No. 61/485,320 filed on May 12, 2011.

FEDERALLY SPONSORED RESEARCH OR DEVELOPMENT

This invention was made with government support under an award provided by the U.S. Department of Energy, Award No. DE-EE0003044. The government has certain rights in the invention.

BACKGROUND

The increasing cost of fossil fuel and environmental concerns have stimulated worldwide interest in developing alternatives to petroleum-based fuels and chemicals. Biomass materials have proven to be a possible renewable alternative for these products.

The production of liquid fuels and chemicals from lignocellulosic materials has received significant attention lately as a non-food feedstock alternative. The most promising of these feedstocks include (1) agricultural wastes, such as bagasse, corn and soybean stover, and straws from wheat, rice, barley, and oats, (2) grasses, such as switch grass, miscanthus, cord grass, and reed canary grass, (3) wood products, such as forest residues, pulping residues, saw dust, and specialty wood crops (e.g., aspen wood), (4) algae-derived biomass, including carbohydrates and lipids from microalgae and macroalgae, and (5) proposed energy crops, such as sweet sorghum.

Lignocellulosic biomass includes three major components. Cellulose—a primary sugar source for bioconversion processes—includes high molecular weight polymers formed of tightly linked glucose monomers. Hemicellulose—a secondary sugar source—includes shorter polymers formed of various sugars. Lignin—the backbone to which cellulose and hemicellulose are bound—is made up of phenylpropanoic acid moieties polymerized in a complex three dimensional structure. The combination of these three components provides a lignocellulosic composition of roughly 30-50% cellulose, 15-35% hemicellulose, and 25-35% lignin, by weight.

Very few cost-effective processes currently exist for efficiently converting cellulose, hemicellulose and lignin to components better suited for producing fuels, chemicals, and other products. This is generally because each of the lignin, cellulose and hemicellulose components demands distinct processing conditions, such as temperature, pressure, catalysts, reaction time, etc., in order to effectively break apart its polymer structure. Due to this distinctness, most processes are only able to convert specific fractions of the biomass, such as the cellulose and hemicellulose components, leaving the remaining components behind for additional processing or alternative uses.

Recent developments involving the catalytic conversion of biomass using aqueous-phase reforming (APR), hydrodeoxygenation (HDO), and other catalytic bioreforming processes, have shown great promise in their ability to convert a wide range of biomass-derived feedstocks to liquid fuels and chemicals. APR and HDO are catalytic reforming processes capable of generating hydrogen and hydrocarbons from oxygenated hydrocarbons without a significant disruption of the carbon backbone. The oxygenated hydrocarbons may include starches, mono- and poly-saccharides, sugars, sugar degradation products, and sugar alcohols, as well as other polyols, organic acids, furfurals, phenols, cresols and other degradation products typically produced by lignocellulosic deconstruction technologies.

Various APR methods and techniques are described in U.S. Pat. Nos. 6,699,457; 6,964,757; 6,964,758; and 7,618,612 (all to Cortright et al., and entitled "Low-Temperature Hydrogen Production from Oxygenated Hydrocarbons"); U.S. Pat. No. 6,953,873 (to Cortright et al., and entitled "Low-Temperature Hydrocarbon Production from Oxygenated Hydrocarbons"); and U.S. Pat. Nos. 7,767,867 and 7,989,664; and U.S. Patent Application Ser. No. 2011/0306804 (to Cortright, and entitled "Methods and Systems for Generating Polyols"). Various APR and HDO methods and techniques are described in U.S. Pat. Nos. 8,053,615; 8,017,818; and 7,977,517; and U.S. Patent Application Ser. Nos. 2011/0257448; 2011/0245543; 2011/0257416; and 2011/0245542 (all to Cortright and Blommel, and entitled "Synthesis of Liquid Fuels and Chemicals from Oxygenated Hydrocarbons"); U.S. Patent Application Ser. No. 2009/0211942 (to Cortright, and entitled "Catalysts and Methods for Reforming Oxygenated Compounds"); U.S. Patent Application Ser. No. 2010/0076233 (to Cortright et al., and entitled "Synthesis of Liquid Fuels from Biomass"); International Patent Application No. PCT/US2008/056330 (to Cortright and Blommel, and entitled "Synthesis of Liquid Fuels and Chemicals from Oxygenated Hydrocarbons"); and commonly owned co-pending International Patent Application No. PCT/US2006/048030 (to Cortright et al., and entitled "Catalyst and Methods for Reforming Oxygenated Compounds"), all of which are incorporated herein by reference.

The first step in the process of converting lignocellulosic biomass to a useable feedstock involves the deconstruction of the complex polymeric matrices of the cellulosic, hemicellulosic and lignin material. This is typically accomplished using the following methods, either alone or in combination: (1) thermochemical treatment using a mineral acid, strong base, water at autohydrolysis conditions, gas catalyst, oxidation catalyst, and/or an organic solvent (2) enzymatic hydrolysis, and more recently (3) catalytic biomass deconstruction.

Acid hydrolysis is one type of thermochemical treatment. In acid hydrolysis, the feedstock is subjected to steam and a mineral acid (e.g., sulfuric acid, hydrochloric acid, or phosphoric acid) to hydrolyze the cellulose and hemicellulose to their monomeric components. For cellulose, this is glucose, while hemicellulose is hydrolyzed to xylose, galactose, mannose, arabinose, acetic acid, galacturonic acid, and glucuronic acid. Sulfuric acid, hydrochloric acid, and phosphoric acid are the three most common mineral acids used for this process. Once complete, the resulting slurry contains the mineral acid, as well as residual or unreacted fiber from lignin, and an aqueous solution of the desired sugars and other hydrolysate products, such as organic acids, including primarily acetic acid, but also formic acid, propionic acid, malic acid, citric acid, oxalic acid, lactic acid, butyric acid, valeric acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, hexanoic acid, heptanoic acid, salts, and other degradation products, including furfurals, phenols, and cresols.

The cost of fresh mineral acid is a significant operational cost for acid hydrolysis of biomass.

Enzymatic hydrolysis typically involves a thermochemical pretreatment followed by hydrolysis with cellulose enzymes. The thermochemical pretreatment is used to increase the surface area of the cellulose material to allow enzyme penetration. When compared to acid hydrolysis alone, the thermochemical pretreatment steps are generally milder (e.g., lower mineral acid concentrations, shorter treatment times, etc.). After acid pretreatment, base is added to the solution to raise the pH to a range in which the enzyme is active and, in the process, the mineral acid is converted into a mineral salt. Similar to the acid hydrolysis process, the hemicellulose is hydrolyzed by the mineral acid to xylose, galactose, mannose, arabinose, acetic acid, galacturonic acid, and glucuronic acid. The cellulose is hydrolyzed by the enzymes to glucose. The cost of enzymes and base are significant operational costs for enzymatic hydrolysis of biomass.

Catalytic biomass deconstruction involves the use of a heterogeneous catalyst to hydrolyze the cellulose, hemicellulose and, in some instances, the lignin to water-soluble oxygenated hydrocarbons. The oxygenated hydrocarbons include carbohydrates, starches, polysaccharides, disaccharides, monosaccharides, sugars (including glucose, xylose, galactose, mannose, arabinose), sugar degradation products (e.g., hydroxymethyl furfural (HMF), levulinic acid, formic acid, and furfural), sugar alcohols, alditols, polyols, diols, alcohols, ketones, cyclic ethers, esters, carboxylic acids, aldehydes, phenols, cresols and other oxygenated hydrocarbon species.

Regardless of the deconstruction process used, the resulting hydrolysate stream is likely to contain the desired sugars, organic acids and other oxygenated hydrocarbons derived from hemicellulose, cellulose, and lignin, as well as contaminants, such as mineral salts, mineral acids, other solvents used in deconstruction, terpenoids, stilbenes, flavonoids, proteinaceous materials, metal impurities, ash and other organic products. The glucose can be readily converted to butanol using bacteria or ethanol using conventional yeast fermentation techniques. The pentose sugars may also be converted to a wide variety of fuels and chemicals using recombinant yeast, bacteria, or algae. The remaining organic and inorganic materials may be used for fertilizer or other applications, while the mineral acids and mineral salts may be recycled for continued use in the purification system.

The presence of the organic acids, their corresponding salts and other oxygenated hydrocarbons in a hydrolysate stream are deleterious to fermentation and other biological processes. In particular, the presence of these compounds can inhibit effective yeast, bacterial, or algal activity, resulting in reduced yields or a corresponding increase in the amount of yeast, bacteria, algae or enzymes required. It is therefore imperative for fermentation and other biological processes to remove organic acids and other non-sugar compounds to produce a feedstock stream containing primarily sugar. The result is a reduction in overall product yield from the biomass due to the removal of the organic acids and other oxygenated hydrocarbons from the fuel conversion process.

The APR and HDO technologies, on the other hand, are able to convert mixed feedstock streams containing not only sugars and sugar alcohols, but also organic acids, and other oxygenated hydrocarbons. Contaminants, such as mineral salts, mineral acids, proteinaceous materials, ash and other organic products, however, can decrease catalyst lifetime and functionality. It is therefore desirable to remove these contaminants and provide a feedstock stream containing the sugars, as well as the organic acids and other oxygenated hydrocarbons derived from the lignocellulosic conversion process.

SUMMARY

The invention provides methods for purifying a biomass-derived feedstock stream. The method generally involves contacting a feedstock stream comprising water, contaminants and biomass-derived oxygenated hydrocarbons with an anion exchange unit and a cation exchange unit, for a time sufficient to remove a significant portion of the contaminants from the feedstock stream to produce a product stream. The anion exchange unit may be modified with one or more organic acids selected from the group consisting of acetic acid, formic acid, propionic acid, malic acid, citric acid, oxalic acid, lactic acid, butyric acid, valeric acid, hexanoic acid, heptanoic acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, salts thereof and mixtures thereof. The product stream comprises water, one or more organic acids, and one or more biomass-derived oxygenated hydrocarbons selected from the group consisting of carbohydrates, starches, polysaccharides, disaccharides, monosaccharides, sugars, sugar alcohols, sugar degradation products, alditols, polyols, triols, diols, mono-oxygenates, phenols, cresols, and mixtures thereof. In one embodiment, the method for purifying a biomass-derived feedstock stream includes concentrating the product stream by evaporation.

One aspect of the invention is the form of the cation exchange unit. In one embodiment, the form of the cation exchange unit is selected from the group consisting of hydrogen, sodium, potassium, calcium, ammonium, and mixtures thereof.

The contaminants in the feedstock stream may include one or more species selected from the group consisting of mineral salts, mineral acids, terpenoids, stilbenes, flavonoids, proteinaceous materials, metal impurities, ash, and mixtures thereof. In some embodiments, greater than 80%, 90%, 95%, or essentially all of the contaminants are removed from the feedstock stream.

Another aspect of the invention is the anion and cation exchange units. In one embodiment, the anion exchange unit and the cation exchange unit are admixed. In another embodiment, the feedstock stream contacts at least one of the anion exchange unit and the cation exchange unit in a column. In another embodiment, the feedstock stream contacts at least one of the anion exchange unit and the cation exchange unit in the form of a slurry. In still another embodiment, the anion exchange unit or the cation exchange unit may be regenerated with one or more regenerants, thereby producing an effluent stream comprising the contaminants.

In one embodiment, the feedstock stream further comprises an insoluble fraction, the method further comprising filtering the feedstock stream to remove the insoluble fraction prior to contacting the feedstock stream with the anion exchange unit and cation exchange unit. The biomass-derived oxygenated hydrocarbon may be derived from at least one member selected from the group consisting of hemicellulose, cellulose, lignin, corn stover, wheat straw, barley straw, canola straw, oat straw, rice straw, soybean stover, grass, bagasse, switch grass, miscanthus, sorghum, wood, saw dust, beet pulp, algae, forest waste, and agricultural waste. The organic acid may be derived from a lignocellulosic hydrolysate or from one or more of the biomass-derived oxygenated hydrocarbons.

Another aspect of the invention is a method for purifying a biomass-derived feedstock stream. The method generally involves: (1) providing a feedstock stream comprising water, contaminants and biomass-derived oxygenated hydrocarbons; (2) providing an anion exchange unit comprising an anion resin modified with one or more organic acids selected from the group consisting of acetic acid, formic acid, propionic acid, malic acid, citric acid, oxalic acid, lactic acid, butyric acid, valeric acid, hexanoic acid, heptanoic acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, salts thereof and mixtures thereof; (3) providing a cation exchange unit comprising a cation resin modified with a modifier; and (4) contacting the feedstock stream with the anion exchange unit and the cation exchange unit, for a time sufficient to remove a significant portion of the contaminants from the feedstock stream, thereby producing a first product stream comprising water, one or more organic acids, and one or more biomass-derived oxygenated hydrocarbons selected from the group consisting of carbohydrates, starches, polysaccharides, disaccharides, monosaccharides, sugars, sugar alcohols, sugar degradation products, alditols, polyols, triols, diols, mono-oxygenates, phenols, cresols, and mixtures thereof.

In certain embodiments, the method includes any of the following further steps: (5) contacting the anion resin and cation resin with water for a time sufficient to produce a second product stream comprising one or more biomass-derived oxygenated hydrocarbons selected from the group consisting of carbohydrates, sugars, sugar alcohols, and sugar degradation products; (6) regenerating the anion resin with an anion regenerant, and the cation resin with a cation regenerant, to produce a concentrated anion regenerant stream and a concentrated cation regenerant stream; (7) rinsing the anion exchange resin and the cation exchange resin with water to produce a dilute anion regenerant stream and a dilute cation regenerant stream; or (8) contacting the anion resin and cation resin with a stream selected from the group consisting of the feedstock stream, second product stream, or a mixture thereof, to produce a third product stream comprising one or more biomass-derived oxygenated hydrocarbons.

In one embodiment, the contaminants comprise one or more species selected from the group consisting of mineral salts, mineral acids, terpenoids, stilbenes, flavonoids, proteinaceous materials, metal impurities, ash, and mixtures thereof. The modifier may be selected from the group consisting of hydrogen, sodium, potassium, calcium, ammonium, and mixtures thereof, and the anion regenerant may be derived from the product stream.

Another aspect of the invention is a method for purifying a biomass-derived feedstock stream. The method generally involves contacting a feedstock stream comprising water, biomass-derived oxygenated hydrocarbons, and one or more contaminants with an anion exchange unit modified with one or more organic acids, and a cation exchange unit, for a time sufficient to remove a significant portion of the contaminants from the feedstock stream, thereby producing a product stream. The contaminants are selected from the group consisting of mineral salts, mineral acids, terpenoids, stilbenes, flavonoids, proteinaceous materials, metal impurities, ash, and mixtures thereof. The product stream comprises water, one or more organic acids, and one or more biomass-derived oxygenated hydrocarbons selected from the group consisting of carbohydrates, starches, polysaccharides, disaccharides, monosaccharides, sugars, sugar alcohols, sugar degradation products, alditols, polyols, triols, diols, mono-oxygenates, phenols, cresols, and mixtures thereof. In one embodiment, the method further includes regenerating the anion exchange unit or the cation exchange unit with one or more regenerants, thereby producing an effluent stream comprising the contaminants.

In one embodiment, the one or more organic acids is selected from the group consisting of acetic acid, formic acid, propionic acid, malic acid, citric acid, oxalic acid, lactic acid, butyric acid, valeric acid, hexanoic acid, heptanoic acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, salts thereof and mixtures thereof. The cation exchange unit may be in a form selected from the group consisting of hydrogen, sodium, potassium, calcium, ammonium, and mixtures thereof.

DETAILED DESCRIPTION

Figure 1:
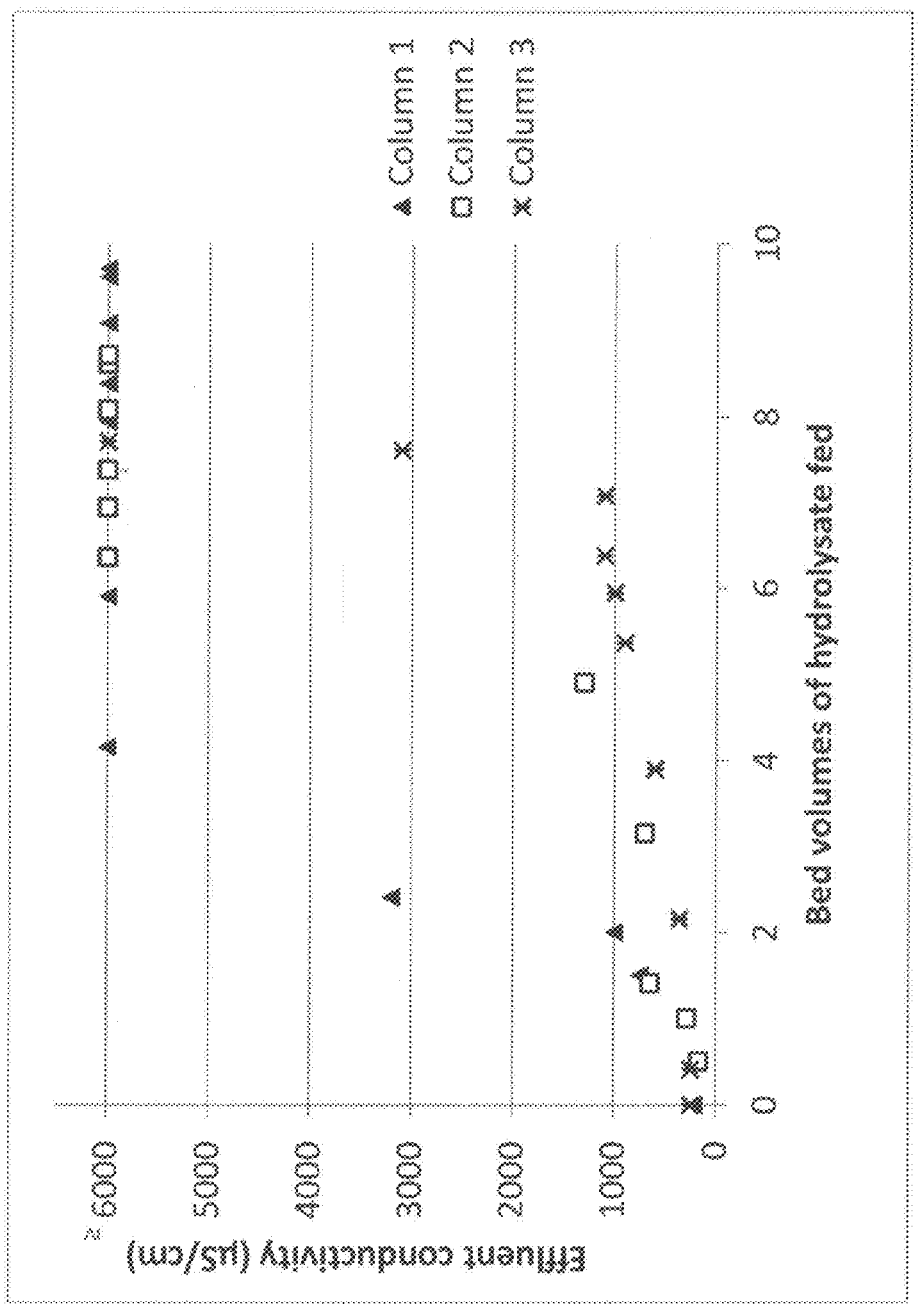
FIG. 1 is a graph illustrating a breakthrough curve in which corn stover hydrolysate was fed to a series of three columns, the first is packed with cation resin in the hydrogen form, the second is packed with anion resin in the acetate form, and the third is packed with a mixed resin containing an anion exchange resin in acetate form and a hydrogen form cation exchange resin.

The present invention relates to processes for purifying an aqueous feedstock stream derived from the conversion of biomass to oxygenated hydrocarbons. The invention includes methods for removing mineral acids, mineral salts, and contaminants (e.g., metal impurities, terpenoids, stilbenes, flavonoids, proteinaceous materials, ash and other organic products), from a lignocellulosic feedstock stream containing oxygenated hydrocarbons, such as sugar, sugar alcohols, sugar degradation products, organic acids, furfurals, phenols, cresols and other lignin, cellulose and hemicellulose derivatives and degradation products.

As used herein, the term "biomass" refers to, without limitation, organic materials produced by plants (such as leaves, roots, seeds and stalks), and microbial and animal metabolic wastes. Common biomass sources include: (1) agricultural residues, such as corn stalks, straw, seed hulls, sugarcane leavings, bagasse, nutshells, and manure from cattle, poultry, and hogs; (2) wood materials, such as wood or bark, sawdust, timber slash, and mill scrap; (3) municipal waste, such as waste paper and yard clippings; (4) algae-derived biomass, including carbohydrates and lipids from microalgae (e.g., *Botryococcus braunii, Chlorella, Dunaliella tertiolecta, Gracilaria, Pleurochyrsis carterae*, and *Sargassum*) and macroalgae (e.g., seaweed); and (5) energy crops, such as poplars, willows, switch grass, miscanthus, sorghum, alfalfa, prairie bluestream, corn, soybean, and the like. The term also refers to the primary building blocks of the above—lignin, cellulose, hemicellulose, carbohydrates, etc.

The present invention involves the use of both anion exchange resins and cation exchange resins to achieve separation of the mineral salts, mineral acids, and contaminants from the desired oxygenated hydrocarbons. The anion exchange resins are modified with an organic acid that enables the anions on the resin to exchange anions with mineral acids and a portion of the contaminants in the feedstock stream. The cation exchange resins are modified to a hydrogen form, which enables the cations on the resin to exchange cations with a portion of the contaminants in the feedstock stream. During normal service oxygenated hydrocarbons including the sugars, sugar alcohols, organic acids, furfurals, phenols and cresols are absorbed to the resin such that the resin is saturated with regard to oxygenated hydrocarbons.

The cation exchange resin can be either a weak or strong acid cation in hydrogen, sodium, potassium, calcium, ammonium, or other forms. By a strong acid cation exchange resin, it is meant a resin with a polymeric structure comprising a strong acid functional group (e.g., R—$SO_3H$). By a weak acid cation exchange resin, it is meant a resin with a polymeric structure comprising a weak acid functional group (e.g., R—COOH). The result is that oxygenated hydrocarbons pass through the ion exchange units and elute from the system, while the mineral salts, contaminants, and their anions and cations are retained. By hydrogen form, it is meant that the cation exchange resin is structured so that it is able to exchange hydrogen protons for those cations in the feedstock stream having a higher affinity for the resin. For example, a hydrogen form cation exchange resin is able to remove contaminants, such as potassium, calcium, magnesium, sodium, and other cations present in the feedstock stream. Removal of these contaminants reduces the likelihood of precipitation of compounds of low solubility, for example calcium hydroxide and calcium sulfate. Commercial cation resins are usually shipped in $Na^+$ form and are converted to hydrogen form using a strong acid such as 1 M HCl or $H_2SO_4$. If a salt solution is desired, the cation can be left in $Na^+$ form, or converted into an alternate form such as $K^+$ or $NH_4^+$.

Converting the $Na^+$ form cation exchange resin to $H^+$ can be readily accomplished by standard methods (Purolite Company, 2008). For example, $Na^+$ form resin can be contacted with a high molarity solution of strong mineral acid, such as 2 M HCl, at ambient temperature and pressure for at least an hour. Due to the high concentration of strong mineral acid, $H^+$ from the solution displaces the $Na^+$ on the resin. The exchanged resin is then separated from the solution and washed with deionized water to remove any entrained acid. Similarly if a salt form resin is desired, the cation resin can be converted to the desired form by contacting it with a high molar solution of mineral salt containing the desired cationic form, followed by a separation of the resin from the solution and washing with deionized water.

The anion exchange resin is modified to promote the removal of the mineral salts and contaminants from the feedstock solution without also removing the desired oxygenated hydrocarbons (e.g., sugars, organic acids, etc.). In one embodiment, the anion exchange resin is modified using an organic acid, such as an acetic acid, formic acid, propionic acid, malic acid, citric acid, oxalic acid, lactic acid, butyric, acid, valeric acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, hexanoic acid, heptanoic acid, salts of the foregoing, or mixtures of the foregoing. Anion resins are usually shipped in $Cl^-$ form and can be converted using standard procedures well known in the art, with the exception that one of the above acids or their salts are used in place of sodium hydroxide or other alkaline materials. Alternatively, the anion resin can be converted into a mixed organic acid form using two or more of the above acids or salts.

In one embodiment of the invention, the organic acids or salts may be derived from other processes. For example, acetic acid, formic acid, propionic acid, malic acid, citric acid, and oxalic acid are several organic acids derived from the hydrolysis of lignocellulosic feedstocks. In this instance, the organic acid (such as acetic acid) can be separated from the feedstock stream and/or product stream using common separation techniques know in the art, and collected for use in preparing the organic acid form of the anion exchange resin.

Alternatively, the organic acids may originate from other downstream processes capable of converting the product stream to higher valued oxygenated hydrocarbons. For example, the organic acids may include acetic acid, lactic acid, butyric acid, valeric acid, hexanoic acid, and heptanoic acid derived from the conversion of water-soluble oxygenated hydrocarbons as described in U.S. Pat. Nos. 7,767,867 and 7,989,664; and U.S. Patent Application Ser. No. 2011/0306804 all to Cortright, and entitled "Methods and Systems for Generating Polyols", which are incorporated herein by reference. In this instance, the oxygenated hydrocarbons in the product stream of the present invention are collected and further processed over a catalyst(s) in a manner similar to that described in U.S. Pat. Nos. 7,767,867 and 7,989,664; and U.S. Patent Application Ser. No. 2011/0306804. The resulting conversion products can then be separated, using common separation techniques know in the art, to provide the organic acids described above.

The anion exchange resin may originally be a weak base or a strong base anion exchange resin. By a weak base anion exchange resin, it is meant a resin with a polymeric structure comprising a weak base functional group. A common weak base functional group found in weak base anion exchange resins is a tertiary amine Amines such as trialkyl amines and pyridine are found commonly in weak base anion exchange resins. In each instance, a hydroxide group on the resin is replaced by the conjugate of the desired organic acid to provide the necessary functionality according to the present invention.

Alternatively, the anion exchange resin may include a strong base anion exchange resin. By a strong base anion exchange resin, it is meant a resin with a polymeric structure comprising a strong base functional group. A common strong base functional group found in strong base anion exchange resins is a quaternary amine, although it should be appreciated that other functional groups may be used. The strong base anion exchange resin may be a Type I or Type II (Dianion Manual of Ion Exchange Resins and Synthetic Adsorbent, Mitsubishi Chemical Corporation, $2^{nd}$ edition, 1995) strong base anion exchange resin. Type I strong base anion exchange resins comprise a stronger base functional group than Type II resins. Typically, a Type II resin comprises a quartenary ammonium functional group where one of the four nitrogen substituents comprises an aminoethanol group. As with the weak base anion exchange resins, hydroxide groups on the resin are replaced by the conjugate of the desired organic acid to provide the necessary functionality according to the present invention.

The common structure for exchange resins involves copolymers of styrene and divinyl benzene. However, any typical polymer or cross-linking agent common to exchange resins can be used. For example, anion exchange resins may also be formed using an acrylic polymeric support. A polymeric backbone can also be formed using various levels of cross-linking agent to control the porosity of the polymeric structure.

The exchange resins (whether anion or cation) may be macroporous, i.e., containing discrete pores, microporous (e.g., gel resins), or may contain both macroporous and microporous elements. Exchange resins may be prepared to contain a narrow range of particle shape and size or a wide range of particle shape and sizes. The total operating capacity of the exchange resin may vary depending on the process used to prepare the resin. Furthermore, exchange resins can vary depending on the nature of the polymeric structure, supplier, lots, synthesis methods, process parameters, degree of crosslinking, or functional group. This results in resins that differ in certain parameters such as pressure drop, swelling and shrinking, moisture holding capacity, diameter, porosity, thermal stability, physical stability, and the like. It should be understood that the invention is not limited by the specific physical and chemical properties of the resin employed.

The aqueous feedstock stream used in the present invention contains mineral salt(s), mineral acid(s), contaminant(s), and oxygenated hydrocarbons. The mineral salts and mineral acids generally originate from the reagents added during deconstruction of biomass and subsequent pH adjustment, and are carried into the aqueous feedstock stream. Regardless of its source, the mineral acid may be, but is not limited to, sulfuric acid, sulfurous acid, hydrochloric acid, or phosphoric acid, and salts thereof. Contaminants will typically include ash components, such as calcium, aluminum, potassium, sodium, magnesium, ammonium, chloride, sulfate, sulfite, thiol, silica, copper, iron, phosphate, carbonate, and phosphorous, as well as color bodies (e.g., terpenoids, stilbenes, flavonoids), proteinaceous materials and other inorganic or organic products.

The oxygenated hydrocarbons generally include water-soluble oxygenated hydrocarbons and, in some instance, longer chain oxygenated compounds that segregate from an aqueous phase. Water-soluble oxygenated hydrocarbons include monosaccharides, disaccharides, oligosaccharides, polysaccharides, sugars, sugar alcohols, sugar degradation products, organic acids, alditols, ethanediol, ethanedione, propanol, methanol, acetol, pentanone, propanediol, glycerol, acetone, glyceraldehyde, dihydroxyacetone, butanediols, aldotetroses, aldopentoses, aldohexoses, ketotetroses, ketopentoses, ketohexoses, alditols, furfurals, hydroxymethyl furfural, cresols, phenols, dissolved lignin, hemicellulosic derivatives, cellulosic derivatives, lignocellulosic derivatives, starches, polyols and the like. In one example, the oxygenated hydrocarbon includes sugars, sugar degradation products, sugar alcohols, saccharides, organic acids, phenols, cresols, furfurals, hydroxymethyl furfural, and other polyhydric alcohols. Sugars may include glucose, fructose, sucrose, cellobiose, maltose, lactose, mannose, galactose, arabinose or xylose. Sugar degradation products may include hydroxymethyl furfural (HMF), levulinic acid, formic acid, and furfural. Sugar alcohols may include arabitol, erythritol, glycerol, isomalt, lactitol, malitol, mannitol, sorbitol, xylitol, ribitol, or glycol. The organic acids may include acetic acid, propionic acid, galacturonic acid, formic acid, malic acid, citric acid, oxalic acid, lactic acid, butanoic acid, pyruvic acid, malonic acid, tautaric acid, glucuronic acid or a combination thereof.

The feedstock stream is preferably substantially free of undissolved or suspended solids. This may be achieved by filtration, centrifugation, or other processes familiar to those skilled in the art for removing fiber solids or suspended solids from aqueous streams. Optionally, the feedstock stream can be concentrated, for example, by evaporation or with membranes, or the like. It is also contemplated that a portion of the mineral acid is removed from the feedstock stream prior to feeding it to the anion exchange unit, for example, by overliming, chemical precipitation, chromatographic separation or other means.

The aqueous feedstock stream is preferably at a temperature of about 20° C. to about 200° C., or any temperature there between. More preferably, the temperature is about 25° C. to about 195° C., or about 30° C. to about 170° C., or about 35° C. to about 145° C., or about 40° C. to about 100° C., 45° C. to about 75° C., or about 55° C. to about 70° C., or any temperature there-between. For example, the temperature may be 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200° C., or any temperature there-between.

In one embodiment of the invention, the process includes an anion exchange unit and a cation exchange unit to achieve separation of the mineral salts, mineral acids, and contaminants from the aqueous feedstock stream. According to this embodiment, the aqueous feedstock stream is fed to the cation exchange unit. The cation exchange unit uses a hydrogen form cation exchange resin to bind cations in the contaminants. As the feedstock stream passes through the resin bed, the contaminants diffuse into the resin and are exchanged or adsorbed on the resin. In the cation exchange unit, sodium, calcium, magnesium and other cations will replace the hydrogen ions on the resin due to their greater affinity for the resin than the hydrogen ion. The hydrogen ions displaced from the resin cause a drop in the solution pH to a level of about 1.5-3.5. Thus, neutral salts are changed to their corresponding mineral acids. Proteinaceous compounds, at low pH, may be sorbed onto the cation resin either by ion exchange or adsorption on the resin matrix.

The resulting effluent stream from the cation exchange unit containing the oxygenated hydrocarbons is then fed to the anion exchange unit comprising an anion exchange resin bed that binds a portion of the mineral salts, contaminants and their anions. In typical applications, mineral salts, organic acids and color bodies diffuse into the resin and replace the hydroxide ions on the resin due to their greater affinity for the resin than the hydroxide ion. Because the anion exchange resin has been modified by the organic acid in the present invention, the organic acids and other oxygenated compounds (including sugars) will have a low affinity for the resin and are collected in a low-affinity effluent stream.

The effluent stream obtained from the anion exchange unit is a product stream, which is essentially free of mineral salts, mineral acids, and contaminants, but includes the desired oxygenated hydrocarbons. It should be appreciated that the present invention may also be practiced in a manner wherein the feedstock stream is first passed through the anion exchange unit and then the cation exchange unit. The system may also be designed to include additional exchange units to allow for multiple passes of the feedstock stream. The exchange units may also be organized to allow for alternating cation and anion exchange processing through the multiple units. The system may also be designed to include recycle of streams from the regeneration to reduce the loss of hydrolysate during regeneration.

The cation exchange resin and anion exchange resin are typically packed in vertical columns, horizontal beds, or a combination thereof. The cation and anion exchange units may also comprise multiple beds which are arranged in parallel, in series, or may include a combination of beds arranged in series and in parallel. The cation and anion exchange resins may also be combined into a mixed bed, whether packed in vertical columns, horizontal beds, or combined to allow their application in a slurry.

The practice of the invention is not limited by the arrangement of beds. As would be apparent to one of skill in the art, in either case, the volume of the resin bed is typically chosen based on the flow rate and the concentration of the materials in the feedstock stream. The sizing of resin beds may be carried out by combining the data from laboratory, or other experiments, on the aqueous feedstock stream with design principles that are familiar to those skilled in the art.

Preferably, the aqueous feed continues until the mineral salts, mineral acids, or contaminants are leaked into the product stream. This is the point at which, if the feed was continued, a significant concentration of mineral salt, mineral acid, or contaminants would exit the exchange units. The amount of feed that can be added prior to leakage can be determined by bed overload experiments familiar to those skilled in the art. The detection can be carried out by a direct measurement of the amount of mineral salt, mineral acid, or contaminants in the effluent or other indicators known to those of skill in the art, for example, conductivity, pH or other means. Detection of mineral salts, mineral acids, or contaminants can be carried out between beds or columns, on product streams, or any combination thereof. Detection limits of mineral salts, mineral acids, contaminants, or any combination thereof can be used to control operating conditions (e.g., flow rate of feedstock to the system, frequency of regeneration, recycle flow rate, etc.). The liquid held up in the bed is optionally removed by rinsing, draining, or blowing out. The resin beds are then regenerated with a suitable aqueous regenerant.

In one example, the regenerant includes deionized water and another species such as hydrochloric acid, or an alkali such as ammonium hydroxide, potassium hydroxide, or sodium hydroxide to produce a mineral salt. The anion exchange resin may also be regenerated using an organic acid, such as an acetic acid, formic acid, propionic acid, malic acid, citric acid, oxalic acid, lactic acid, butyric acid, valeric acid, hexanoic acid, heptanoic acid, salts of the foregoing, or mixtures of the foregoing. In one embodiment, the regenerant is the same organic acid as that used to prepare the anion exchange resin.

The present invention is not limited by the amount or number of regenerants applied to the exchange units. It will be understood by those skilled in the art that the resin may be regenerated with one or more regenerants introduced in one or more separate steps and that it may be advantageous to use the minimum amount of regenerant necessary to displace a desired amount of bound anions or cations.

Figure 5:
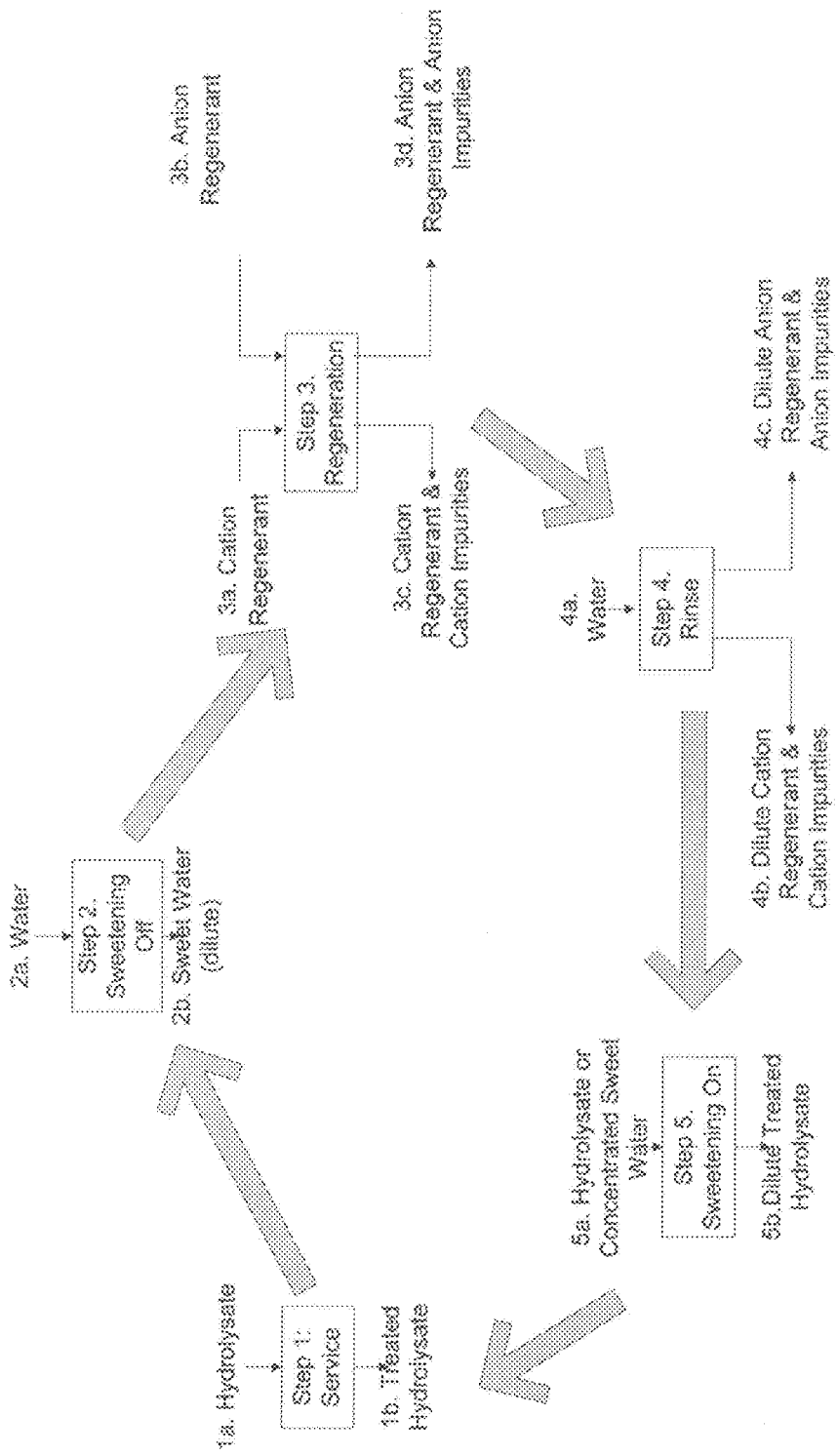
FIG. 5 is a diagram illustrating the cycle of operation for a typical ion exchange system including: Step 1 (normal operation), Step 2 (sweeten off), Step 3 (regeneration/chemical addition), Step 4 (rinse), Step 5 (sweeten on).

FIG. 5 illustrates a purification sequence wherein Step 1 is the service operation and Steps 2 through 5 are regenerative steps including: sweeten off (Step 2), regeneration (Step 3), rinse (Step 4), and sweeten on (Step 5). Following the service operation (Step 1), in Step 2 (sweeten off) the resin is rinsed with water resulting in an effluent containing oxygenated hydrocarbons (primarily sugars) commonly referred to as "sweet water" (2b). In Step 3 cation regenerant (3a) is added to the cation resin and anion regenerant (3b) is added to the anion resin resulting in cation (3c) and anion (3d) regenerant and impurity streams, respectively. The regenerant may be fed to the column(s) in the same direction as the aqueous feed, known as co-current regeneration. Alternatively, the regenerant may be fed counter-current, i.e., in the opposite direction to the aqueous feed. During Step 3, the molar concentration of regenerant in solution is extremely high resulting in a chemical driving force for regenerant to exchange for the mineral impurities in the resin. Two effluents are produced in this step, an effluent from the cation column containing the regenerant and mineral salts released from the cation resin (3c), and an effluent from the anion column containing the regenerant and mineral salts from the anion resin (3d). The mineral salts may be recovered or may be processed and recovered as the mineral salt. The contaminants may be collected and used in other processes or for other purposes, such as fertilizer in agricultural applications.

During Step 4, the cation and anion resins are rinsed with water (4a) to remove regenerant resulting in dilute cation (4b) and dilute anion (4c) regenerant and impurity streams. In Step 5 (sweeten on) hydrolysate (1a) or sweet water (2b) is added back to the resin resulting in dilute treated hydrolysate (5b). As would be apparent to one of skill in the art, in some instances the sweet water (2b) from Step 2 is concentrated before being reintroduced in Step 5 (5a). Concentration can be accomplished by the use of an evaporator, reverse osmosis, or other means. This is commonly done in corn and cane syrup refining to substantially reduce sugar losses in the regeneration process.

Figure 6:
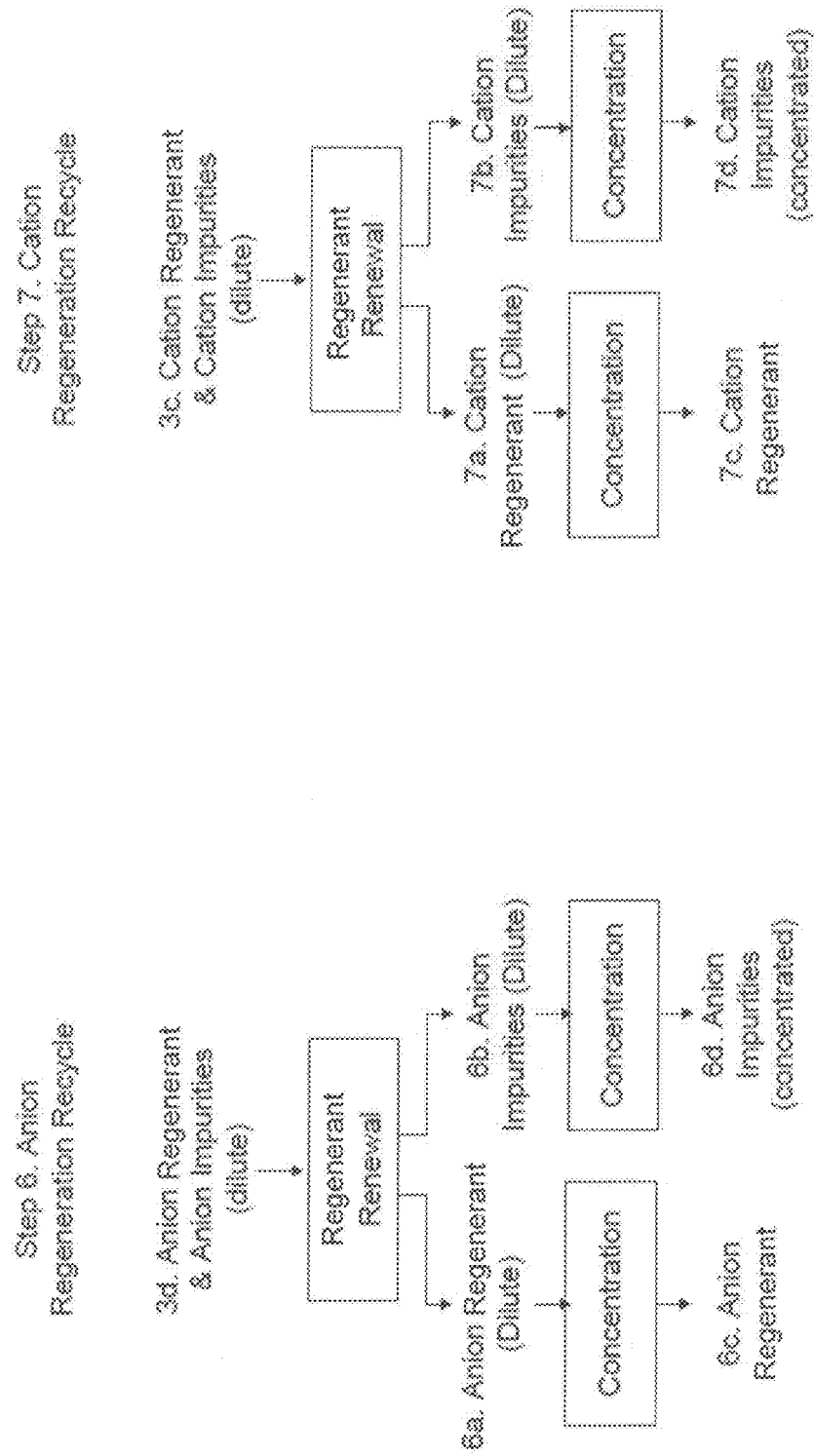
FIG. 6 is a diagram illustrating additional operational steps for an ion exchange (IX) system including: Step 6 (anion regenerant renewal) and Step 7 (cation regenerant renewal), which allows for recycle of mineral acid and base.

FIG. 6 illustrates renewal of the effluent from the regeneration of the anion resin in Step 3. The anion regenerant and anion impurities (3d) is subjected to renewal Step 6, separating the stream into a stream containing dilute regenerant solution (6a) and a stream containing dilute anion impurities (6b). This separation can be accomplished through the use of membranes, distillation, resins, electrodialysis, or other means. The purified regenerant then passes through a concentration step to concentrate it to a high molar concentration (6c) for reuse in regeneration. This concentration step can be accomplished by evaporation, reverse osmosis, nanofiltration, electrodialysis, or other means. Similar processes are practiced in the sugar refinery industry as well as others.

The anion impurity stream (6b) is also concentrated by evaporation, reverse osmosis, nanofiltration, electrodialysis, or other means to a high molar concentration (6d). In the case that the biomass hydrolysate stream originates from dilute acid deconstruction, stream (6d) is primarily sulfuric acid, and it can be recycled for dilute acid hydrolysis. This can substantially reduce the need for fresh sulfuric acid reducing operational costs. It will contain a portion of regenerant and other anion impurities that may improve biomass deconstruction.

Similar to the effluent from the regeneration of the anion column, the effluent from regeneration of the cation column undergoes regenerant renewal and concentration steps (Step 7). Regenerant renewal can be accomplished through the use of membranes, distillation, resins, electrodialysis, or by some other means; concentration can be accomplished by evaporation, reverse osmosis, nanofiltration, electrodialysis, or by some other means. The purified cation regenerant (7c) can then be recycled in regeneration. In the case that biomass hydrolysate stream originates from dilute acid deconstruction, stream (7d) is primarily the base added to adjust the pH between dilute acid pretreatment and enzyme hydrolysis. The base can be recycled, substantially reducing the need for fresh base and the associated costs.

In applications using multiple exchange units, regeneration may be conducted according to a "Merry Go Round" approach. In this approach, the primary pair (anion and cation exchange resins) is regenerated, with the secondary pair moved into primary service. The secondary pair is then replaced with a third pair of freshly regenerated exchange units. Once the new primary pair is exhausted, the process is repeated with the recently regenerated pair being reintroduced as the new secondary pair. Alternative configurations may also include systems utilizing a multiport valve and a number of rotating resin beds, and systems utilizing fixed upflow service dual compartment columns.

The product stream containing the oxygenated hydrocarbons is preferably essentially free of mineral salts, mineral acids, and contaminants. In one embodiment, the product stream has been purified such that greater than 80% of the contaminants contained in the original feedstock stream have been removed. In another embodiment, the product stream has been purified such that greater than 90% of the contaminants contained in the original feedstock stream have been removed. In yet another embodiment, the product stream has been purified such that greater than 95% of the contaminants contained in the original feedstock stream have been removed. In yet a further embodiment, the product stream has been purified such that less than 100 ppm, or 50 ppm, or 25 ppm, or 20 ppm, or 15 ppm, or 10 ppm, or 5 ppm, or 1 ppm, or any amounts there-between, of each mineral salt, mineral acid, or contaminant can be detected in the product stream.

The product stream containing the oxygenated hydrocarbons may optionally be concentrated prior to feeding into other downstream processes. If evaporation is employed, then it should be carried out so that a substantial portion of the oxygenated hydrocarbons are carried forward. Preferably, at least about 90% of the oxygenated hydrocarbons pass through to the downstream operations. More preferably at least about 95%, or even more preferably about 98%, of the oxygenated hydrocarbons pass through.

The process of the invention may be carried out using a simulated moving bed system. Simulated moving bed systems include any continuous chromatographic technique which simulates a flow of a liquid mobile phase moving countercurrent to a flow of a solid stationary phase, i.e., the system simulates movement of the resin bed in a direction opposite to that of the liquid flow. Typically, a simulated moving bed system comprises a set of fixed beds connected in a closed circuit with two or more inlet and two or more outlet streams. The simulated movement may be carried out by periodically shifting four or more flow locations by some fraction of the total bed. A description of the operation of an simulated moving bed system is provided in WO 2006/007691 (Foody and Tolan), to which the reader is directed for reference and which is incorporated by reference. Improved simulated moving bed systems (available for example from Eurodia Industrie S.A., Wissous, France; Applexion S.A., Epone, France; or Amalgamated Research Inc., Twin Falls, Id.) may also be used in the practice of the invention.

The present invention will be further illustrated in the following examples.

EXAMPLES

The following examples are to be considered illustrative of various aspects of the invention and should not be construed to limit the scope of the invention, which are defined by the appended claims.

Example 1

Purification of Corn Stover Hydrolysate

PUROLITE C-150S, a commercial macroporous styrenic strong acid cation exchange resin and PUROLITE A-830, a commercial macroporous acrylic weak acid anion exchange resin, were used to purify a feedstock stream derived from dilute acid and enzymatic hydrolysis of corn stover.

The PUROLITE C-150S cation exchange resin was purchased in the sodium form and was converted to hydrogen form by adding the resin to a glass beaker containing a solution of 2 M HCl. The exchange resin and solution were combined at ambient temperature and pressure, and allowed to soak for an hour, with stirring three to four times over that period with a glass stir rod. Following soaking, the contents were transferred to a glass fritted Buchner funnel and the solution filtered. The exchange resin was then washed five times in the funnel by adding deionized water, stirring with a glass stir rod, then vacuum filtering.

The PUROLITE A-830 anion exchange resin was purchased in chloride form and converted to acetate form by adding the resin to a glass beaker solution of 1 M $HCH_3COOH$ at ambient temperature and pressure and soaked for an hour. Following soaking, the contents were transferred to a glass fritted Buchner funnel and the solution was filtered. The exchange resin was then washed five times in the funnel by adding deionized water, stirring with a glass stir rod, then vacuum filtering.

A corn stover hydrolysate derived from dilute sulfuric acid and enzymatic hydrolysis was purified using the anion and cation exchange resins described above. First, the hydrogen form cation resin was added to a beaker containing the hydrolysate and a magnetic stir bar in a ratio of 0.2 g resin/mL hydrolysate. The beaker was covered in parafilm and placed on a magnetic stirrer at ambient temperature and pressure for a time sufficient to reach equilibrium. The contents were then placed in a syringe and filtered through a syringe filter. In the second step, the liquor was added to a new beaker along with the acetate form anion exchange resin in the ratio of 0.2 g resin/mL initial hydrolysate. The beaker was similarly covered, mixed at ambient temperature and pressure for a time sufficient to reach equilibrium, and then syringe filtered.

The liquid product stream was analyzed. As illustrated in Table 1, all of the measured anionic impurities in the hydrolysate feedstock stream were successfully reduced, except for Si, below detectable levels (less than 5 mg/L) while retaining acetate in solution.

TABLE 1

| Component | Initial Concentration (ppm) | Concentration After Ion Exchange (ppm) |
|---|---|---|
| Si | 49 | 36.9 |
| Cl$^-$ | 287 | BDL |
| NO$_3^{2-}$ | 110 | BDL |
| PO$_4^{2-}$ | 139 | BDL |
| SO$_4^{2-}$ | 5,380 | BDL |
| CH$_3$COO$^-$ | 14,991 | 5,152 |

Example 2

Purification of Corn Stover Hydrolysate Using a Mixed Bed Resin in Packed Columns PUROLITE UCW3700, a gel-type styrenic pre-mixed resin with the cation resin already in hydrogen form and anion in hydroxide form was used. The anion resin was converted to acetate form by adding the mixed bed to a container containing 1 M acetic acid, and soaked for several hours at ambient temperature and pressure, shaking intermediately. Following the soaking period, the contents were transferred to a glass fritted Buchner funnel and the solution was filtered. The resin was washed multiple times by adding deionized water then vacuum filtering, and then packed into a series of three 2 inch ID diameter PVC columns to a height of 10 inches.

A corn stover hydrolysate feedstock derived from dilute sulfuric acid and enzyme hydrolysis was purified using the prepared mixed bed anion and cation exchange resins described above. Feedstock was pumped into the column using an Isametec Ecoline tubing pump at ambient temperature at a rate of about 30-40 mL/min.

The effluent product stream contained purified feedstock until the equilibrium no longer favored the desired exchange or the contact time was insufficient to reach equilibrium. The equilibrium changed due to consumption of the exchange capacity, leading to breakthrough of mineral impurity. FIG. 1 shows a breakthrough curve in which the corn stover hydrolysate was fed to the series of three columns packed with mixed bed resin in acetate form. As exchange capacity became exhausted and contaminants broke through the column, the effluent conductivity increased.

Example 3

Sample and Purification Comparison

Three separate hydrolysate samples were processed for purification. Hydrolysate 1 was a pine hydrolysate produced by dilute acid and enzyme hydrolysis. Hydrolysate 2 was a pine hydrolysate produced by thermochemical treatment and enzyme hydrolysis. Hydrolysate 3 was the same corn stover hydrolysate of Example 2 (produced by dilute sulfuric acid and enzyme hydrolysis).

Figure 2:
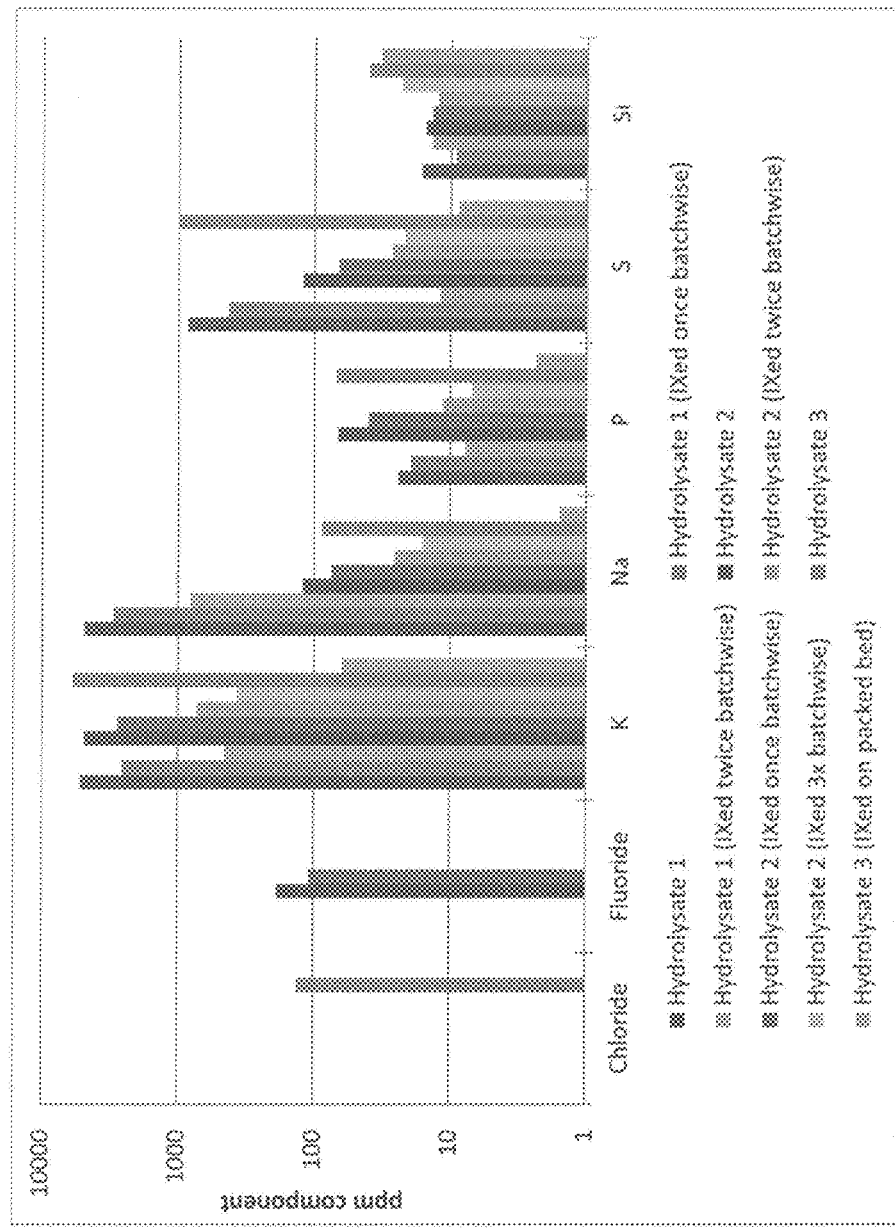
FIG. 2 is a graph illustrating the effectiveness of a mixed bed resin containing an anion exchange resin in acetate form and a hydrogen form cation exchange resin in removing metals from three different hydrolysate samples.
Figure 3:
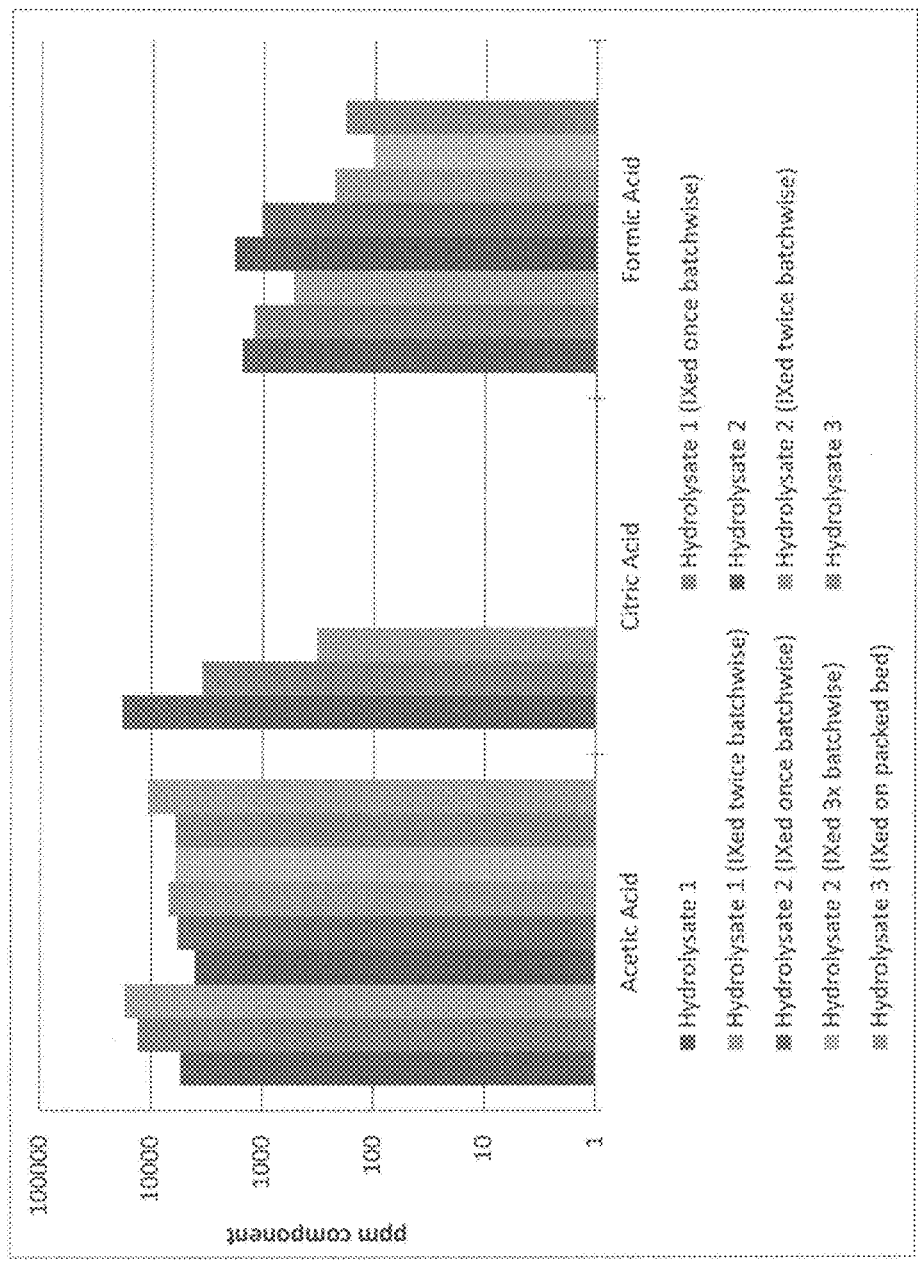
FIG. 3 is a graph illustrating the effectiveness of maintaining acetic acid in the product stream after the treatment of three different hydrolysate samples using a mixed bed resin containing an anion exchange resin in acetate form and a hydrogen form cation exchange resin.

Hydrolysate 1 and 2 were purified using the batch system as described in Example 1, while Hydrolysate 3 was purified using the mixed bed resins packed in columns as described in Example 2. FIGS. 2 and 3 show the effectiveness of the purification processes (batch and packed columns) for certain components. As can be seen in the figures, Na and K levels were reduced by over an order of magnitude. The anionic metal impurities were efficiently removed, with chloride and fluoride reduced to below detectable limits and sulfur, which was originally as high as 1,000 ppm in one sample and mostly in the form of sulfate, reduced to less than 10 ppm. Acetic acid levels increased as other species were exchanged for acetate.

Example 4

Purification of Corn Stover Hydrolysate with Packed Columns in Series

A series of ion exchange resins were packed into 4 inch ID diameter PVC columns to a height of 60 inches. The first column in the series was loaded with a commercial macroporous styrenic strong acid cation exchange resin. The second column was loaded with PUROLITE A-133S, a commercial macroporous acrylic weak acid anion exchange resin. The third column was loaded with PUROLITE UCW3700, a gel-type styrenic pre-mixed resin. The A-133S and UCW3700 resins were converted to acetate form by passing 2.5 bed volumes of 1 M acetic acid through each packed column in parallel. Each column was rinsed in parallel with deionized water.

Figure 4:
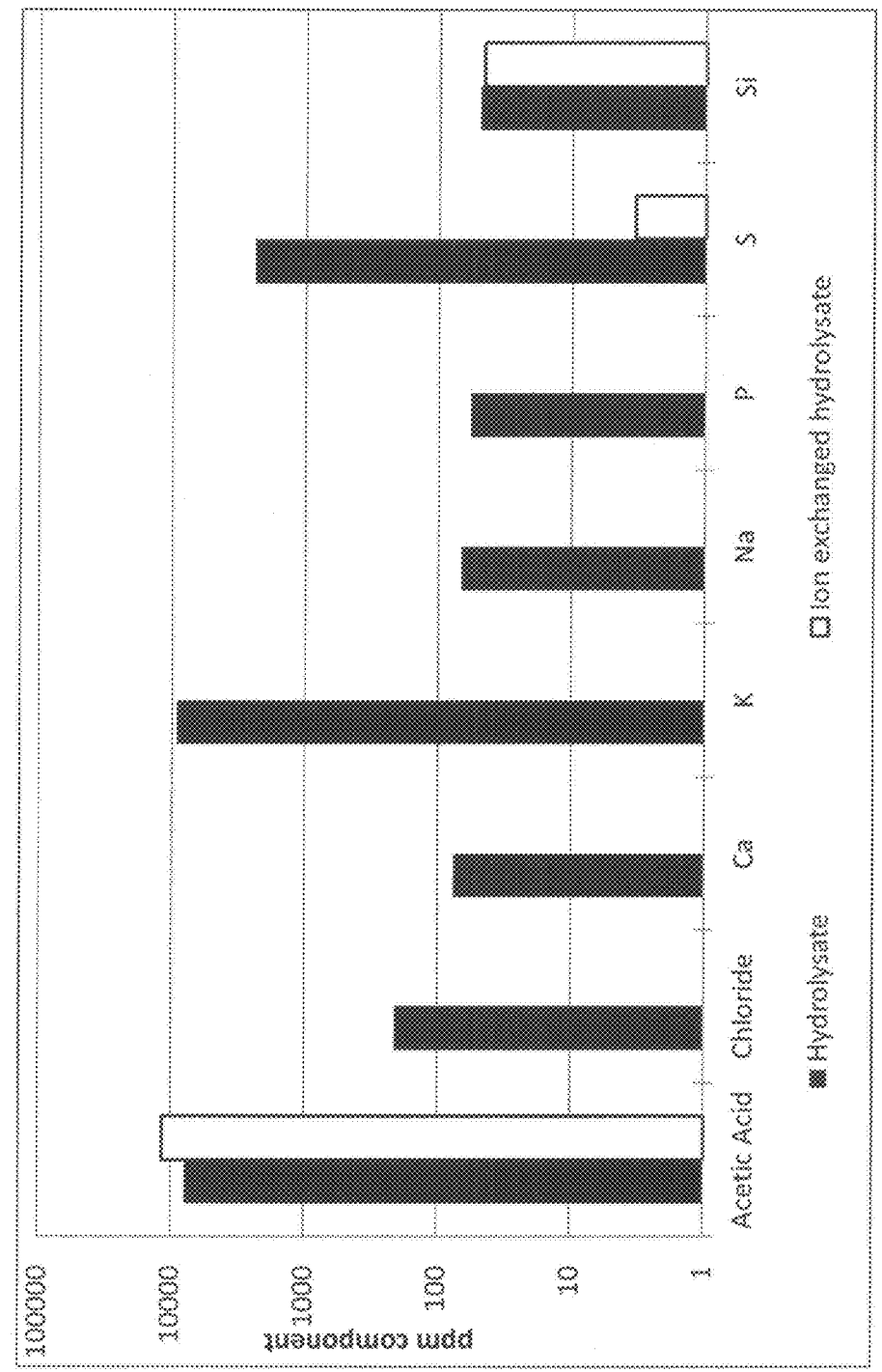
FIG. 4 is a graph illustrating the effectiveness of a series of packed bed columns containing a hydrogen form cation exchange resin, an acetate form anion exchange resin, and a mixed (cation/anion) exchange resin in removing components from a hydrolysate sample.

A corn stover hydrolysate was produced by dilute acid and enzyme hydrolysis. The hydrolysate was then fed through the series of columns described above (first, second, and third columns). Hydrolysate was pumped into the column using a MEC-O-MATIC Dolphin Series peristaltic pump at ambient temperature at a rate of about 190-220 mL/min. After fully sweetening on the series, a sample from the effluent was analyzed. FIG. 4 shows the effectiveness of the purification process for certain components. As can be seen in FIG. 4, alkali levels were reduced to below detectable limits. The anionic metal impurities were efficiently removed, with chloride reduced to below detectable limits and sulfur, which was originally as high as 2,400 ppm and mostly in the form of sulfate, reduced to less than 4 ppm. Acetic acid levels increased as other species were exchanged for acetate.

We claim:

1. A method for purifying a biomass-derived feedstock stream, the method comprising:
   a. providing a feedstock stream having components comprising (i) water, (ii) mineral acids and/or mineral salts, (iii) one or more species of contaminants selected from the group consisting of terpenoids, stilbenes, flavonoids, proteinaceous materials, metal impurities, ash, and mixtures thereof, and (iv) a mixture of oxygenated hydrocarbons comprising one or more biomass-derived organic acids and one or more biomass-derived oxygenated hydrocarbons selected from the group consisting of carbohydrates, starches, polysaccharides, disaccharides, monosaccharides, sugars, sugar alcohols, sugar degradation products, alditols, polyols, triols, diols, mono-oxygenates, phenols, cresols, and mixtures thereof;
   b. providing an anion exchange unit modified with one or more anion modifiers selected from the group consisting of acetic acid, formic acid, propionic acid, malic acid, citric acid, oxalic acid, lactic acid, butyric acid, valeric acid, hexanoic acid, heptanoic acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, salts thereof and mixtures thereof, before contact of the anion exchange unit with components of the feedstock stream;

c. providing a cation exchange unit in a form selected from the group consisting of hydrogen, sodium, potassium, calcium, ammonium, and mixtures thereof;

d. contacting components of the feedstock stream with the anion exchange unit and the cation exchange unit to remove greater than 80% of the mineral salts, mineral acids or contaminants from the feedstock stream, thereby producing a product stream comprising water, greater than 90% of the organic acids from the feedstock stream and greater than 90% of the biomass-derived oxygenated hydrocarbons from the feedstock stream; and e. recycling a portion of the organic acids from the product stream to provide the anion modifier.

2. The method of claim 1 wherein the anion exchange unit and the cation exchange unit are admixed.

3. The method of claim 1 wherein the feedstock stream contacts at least one of the anion exchange unit and the cation exchange unit in a column.

4. The method of claim 1 wherein the feedstock stream contacts at least one of the anion exchange unit and the cation exchange unit in the form of a slurry.

5. The method of claim 1 wherein greater than 90% of the mineral acids, mineral salts or contaminants are removed from the feedstock stream.

6. The method of claim 1 wherein greater than 95% of the mineral acids, mineral salts or contaminants are removed from the feedstock stream.

7. The method of claim 1 wherein essentially all of the mineral acids, mineral salts or contaminants are removed from the feedstock stream.

8. The method of claim 1 further comprising regenerating the anion exchange unit or the cation exchange unit with one or more regenerants, thereby producing an effluent stream comprising the mineral acids, mineral salts or contaminants.

9. The method of claim 1 further comprising concentrating the product stream by evaporation.

10. The method of claim 1 wherein the feedstock stream further comprises an insoluble fraction, the method further comprising filtering the feedstock stream to remove the insoluble fraction prior to contacting the feedstock stream with the anion exchange unit and cation exchange unit.

11. The method of claim 1 wherein the biomass-derived oxygenated hydrocarbon is derived from at least one member selected from the group consisting of hemicellulose, cellulose, lignin, corn stover, wheat straw, barley straw, canola straw, oat straw, rice straw, soybean stover, grass, bagasse, switch grass, miscanthus, sorghum, wood, saw dust, beet pulp, algae, forest waste, and agricultural waste.

12. The method of claim 1 wherein the organic acid is derived from a lignocellulosic hydrolysate.

13. The method of claim 1 wherein the organic acid is derived from one or more of the biomass-derived oxygenated hydrocarbons.

14. A method for purifying a biomass-derived feedstock stream, the method comprising:

a. providing a feedstock stream having components comprising (i) water, (ii) mineral acids and/or mineral salts, (iii) one more species of contaminants selected from the group consisting of terpenoids, stilbenes, flavonoids, proteinaceous materials, metal impurities, ash, and mixtures thereof, and (iv) a mixture of oxygenated hydrocarbons comprising one or more biomass-derived organic acids and one or more biomass-derived oxygenated hydrocarbons selected from the group consisting of carbohydrates, starches, polysaccharides, disaccharides, monosaccharides, sugars, sugar alcohols, sugar degradation products, alditols, polyols, triols, diols, mono-oxygenates, phenols, cresols, and mixtures thereof;

b. providing an anion exchange unit comprising an anion resin modified with one or more anion modifiers selected from the group consisting of acetic acid, formic acid, propionic acid, malic acid, citric acid, oxalic acid, lactic acid, butyric acid, valeric acid, hexanoic acid, heptanoic acid, aconitic acid, caproic acid, 2-furoic acid, vanillic acid, syringic acid, protocatechuic acid, ferulic acid, p-coumaric acid, sinapic acid, gallic acid, glucuronic acid, galacturonic acid, cellobiouronic acid, aldonic acids, aldaric acids, salts thereof and mixtures thereof, before contact of the anion exchange unit with components of the feedstock stream;

c. providing a cation exchange unit comprising a cation resin modified with a cation modifier;

d. contacting components of the feedstock stream with the anion exchange unit and the cation exchange unit to remove greater than 80% of the mineral salts, mineral acids or contaminants from the feedstock stream, thereby producing a first product stream comprising water, greater than 90% of the organic acids from the feedstock stream and greater than 90% of the biomass-derived oxygenated hydrocarbons from the feedstock stream; and e. recycling a portion of the organic acids from the product stream to provide the anion modifier.

15. The method of claim 14, further comprising:

f. contacting the anion resin and cation resin with water to produce a second product stream comprising a portion of the biomass-derived oxygenated hydrocarbons from the feedstock stream.

16. The method of claim 15 further comprising:

g. regenerating the anion resin with an anion regenerant, and the cation resin with a cation regenerant, to produce a concentrated anion regenerant stream and a concentrated cation regenerant stream.

17. The method of claim 16 further comprising:

h. rinsing the anion exchange resin and the cation exchange resin with water to produce a dilute anion regenerant stream and a dilute cation regenerant stream.

18. The method of claim 17 further comprising:

i. contacting the anion resin and cation resin with a stream selected from the group consisting of the feedstock stream, second product stream, or a mixture thereof, to produce a third product stream comprising a portion of the biomass-derived oxygenated hydrocarbons from the feedstock stream.

19. The method of claim 14 wherein the cation modifier is selected from the group consisting of hydrogen, sodium, potassium, calcium, ammonium, and mixtures thereof.

20. The method of claim 16 wherein the anion regenerant is derived from the product stream.

* * * * *